United States Patent [19]
Kubicek

[11] 3,963,785

[45] June 15, 1976

[54] MERCAPTANS BY ADDITION OF HYDROGEN SULFIDE TO OLEFINS IN PRESENCE OF CARBON DISULFIDE

[75] Inventor: Donald H. Kubicek, Bartlesville, Okla.

[73] Assignee: Phillips Petroleum Company, Bartlesville, Okla.

[22] Filed: May 1, 1975

[21] Appl. No.: 573,505

[52] U.S. Cl. .................. 260/609 B; 260/609 R; 260/609 E; 260/609 D
[51] Int. Cl.² .............. C07C 148/00; C07C 149/26; C07C 149/06
[58] Field of Search .............................. 260/609 B

[56] References Cited
UNITED STATES PATENTS

| | | | |
|---|---|---|---|
| 2,402,586 | 6/1946 | Alvarado | 260/609 B |
| 3,036,133 | 5/1962 | Goshorn et al. | 260/609 B |
| 3,214,386 | 10/1965 | Warner et al. | 260/609 B |
| 3,219,709 | 11/1965 | Louthan | 260/609 B |
| 3,221,056 | 11/1965 | Louthan | 260/609 B |
| 3,257,464 | 6/1966 | Buchholz et al. | 260/609 B |
| 3,419,614 | 12/1968 | Doss | 260/609 B |

*Primary Examiner*—Lewis Gotts
*Assistant Examiner*—D. R. Phillips

[57] ABSTRACT

In a method for preparing mercaptans by the addition of hydrogen sulfide to olefins in the presence of sulfactive catalysts a method is provided for increasing the total conversion of reactants to mercaptans by including carbon disulfide in the reaction mixture. In a preferred embodiment carbon disulfide is present in the reaction mixture of hydrogen sulfide and ethylenically unsaturated compounds in an amount in the molar ratio of about 5/1 to about 30/1 hydrogen sulfide to carbon disulfide.

5 Claims, No Drawings

MERCAPTANS BY ADDITION OF HYDROGEN SULFIDE TO OLEFINS IN PRESENCE OF CARBON DISULFIDE

BACKGROUND OF THE INVENTION

This invention pertains to the preparation of mercaptans. In a more specific aspect of this invention it pertains to the preparation of thiols, thioethers and disulfides by the reaction of hydrogen sulfide with ethylenically unsaturated compounds. In another aspect of this invention it pertains to an improvement in the conversion of reactants in the process of preparing mercaptans from the reaction of hydrogen sulfide with ethylenically unsaturated compounds in the presence of a sulfactive catalyst.

It is well known in the art to prepare mercaptans by the addition of hydrogen sulfide to olefins in the presence of a sulfactive catalyst. This reaction has been modified by the use of various promoters for the catalyst and by the presence of modifying compounds along with the reactants. I have discovered that the presence of carbon disulfide in the reaction mixture enhances the conversion of reactants to the desired mercaptan products.

It is, therefore, an object of this invention to provide a method for improving the conversion of hydrogen sulfide and ethylenically unsaturated compound reactants to mercaptan products.

Other aspects, objects and the various advantages of this invention will become apparent upon reading of the specification and the appended claims.

STATEMENT OF THE INVENTION

According to the present invention, in the preparation of mercaptans by contacting a reaction mixture of hydrogen sulfide and ethylenically unsaturated compounds in the presence of a sulfactive catalyst a method for increasing the total conversion of reactants to mercaptans is provided by adding carbon disulfide to the reaction mixture.

The ethylenically unsaturated compounds useful in the practice of this invention include those represented by the following general formula:

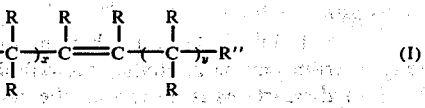

wherein $x$ and $y$ are independently 0 or integers having values of from 1 to 5; wherein the R groups are independently selected from the group consisting of hydrogen and alkyl, cycloalkyl and aryl radicals, or combinations thereof such as alkaryl, aralkyl and the like preferably having 1 to 8 carbon atoms; R' and R'' are independently selected from the group consisting of hydrogen and alkyl radicals having 1 to 5 carbon atoms, and together can form a covalent bond, thus producing a ring, with the proviso that when a covalent bond is formed the sum of $x$ and $y$ is at least 3. The total number of carbon atoms in the ethylenically unsaturated compounds can vary, but generally will not exceed 20.

Representative ethylenically unsaturated compounds of Formula I include: ethylene, propylene, 1-butene, 2-butene, isobutylene, 1-octene, 3-tetradecene, 9-eicosene, 3,5,7-trimethyl-4-decene, cyclopentene, cyclohexene, cyclodecene, cyclohexylethylene, allylcyclopentane, styrene, p-tolylethylene, allyl benzene, 3-butenylbenzene, stilbene, 1,2-dicyclohexylethylene and the like.

The molar ratio of hydrogen sulfide to olefin will generally be within the range of about 0.1/1 to about 20/1 and preferably in the range of about 1/1 to about 5/1.

The molar ratio of hydrogen sulfide to carbon disulfide in the practice of this invention will generally be in the range of from about 5/1 to about 30/1 and preferably in the range of about 15/1 to about 25/1.

If desired, an inert diluent can be used. Suitable diluents include aliphatic, cycloaliphatic and aromatic hydrocarbons such as, pentane, hexane, octane, cyclopentane, cyclohexane, benzene, toluene and xylene. Where a diluent is used, it will generally constitute from about 10 to about 75 weight percent of the solution of the olefin in the diluent. It is currently preferable to carry out the reaction without using a diluent.

Catalysts suitable for use in this invention can be defined as sulfactive hydrogenation catalysts, which definition generally includes the sulfides of Group VI and Group VIII metals such as cobalt, nickel, molybdenum, iron, tungsten, chromium, platinum, etc., either alone or in combination with one another. The catalytic material is usually deposited on a support such as activated carbon, alumina, zirconia, thoria, pumice, silica and silica-alumina. Combinations of nickel or cobalt with molybdenum are generally among the most preferred of such catalysts. Such sulfactive catalysts are well known. Many are commercially available.

Since many of the suitable catalysts are commercially available in the oxide form they can be sulfided prior to use or preferably, employed directly in the oxide form since sulfiding occurs readily in situ under the conditions employed in the present invention. One such commercially available catalyst that is preferred for use in the process of this invention has the following composition: CoO (3–4 percent by weight), $MoO_3$ (15–16 percent by weight), $Na_2O$ (0.4 percent), Fe (0.05 percent), the remainder being alumina. This catalyst is commonly referred to as cobalt molybdate on alumina.

The reactions of this invention can be carried out at temperatures ranging from about 100° to about 350°C and preferably in the range of about 170 to about 300°C. The reactions are conveniently carried out under pressures of from about 100 to about 5000 psig, though it is currently preferable to employ pressures in the range of about 250 to about 750 psig.

The reactions of this invention can be conveniently carried out in continuous or batch reactors, though the process of this invention is especially well suited for continuous reactors. The weight hourly space velocity (weight feed/weight catalyst/hour) of the feed in a continuous system generally is in the range of about 0.1 to about 20 and preferably is about 0.5 to about 10.

The products of reaction can be recovered by well known procedures. For example, gases can be vented, recovered or recycled, if desired, and the product fractionated, crystallized, or subjected to various other separation and recovery procedures to obtain the desired thiols, thioethers and disulfides.

EXAMPLE

The following runs illustrate the preparation of cyclohexyl mercaptan, dicyclohexyl sulfide and dicyclohexyl disulfide from cyclohexene and hydrogen sulfide both by the process of this invention and compared to prior art processes.

A heated, conventional tubular reactor (18 inches long by ½ inch diameter) filled with 80 ml of cobalt molybdate on alumina, and also containing a thermocouple well (18 inches long by ¼ inch diameter) was employed in the following runs. The reactor was first packed with catalyst and heated to about 25°C below the desired reaction temperature. The feed was started and adjusted to the desired feed rate and pressure. The temperature was then adjusted to the desired reaction temperature. The time interval of at least one hour was allowed before sampling to assure equilibration of the system. Samples were taken by passing the effluent through cold traps which were then warmed slowly to vent unreacted hydrogen sulfide. Product analyses were accomplished by gas-liquid chromatography.

Inventive runs 1, 3 and 5 employed a feed consisting of 900 gm cyclohexene, 745 gm hydrogen sulfide and 82 gm carbon disulfide, a pressure of 500 psig and a weight hourly space velocity of 0.8.

Comparative runs 2, 4 and 6 employed a feed consisting of 900 gm cyclohexene and 745 gm hydrogen sulfide, a pressure of 500 psig and a weight hourly space velocity of 0.8.

Table I gives the other run conditions and results.

TABLE I

| Run No. | Temp., °C | Conv., %$^a$ | $CS_2{}^e$ | Products | | |
|---|---|---|---|---|---|---|
| | | | | $CM^b$ | $DCS^c$ | $DCD^d$ |
| 1 (Inventive) | 177 | 70.6 | 4.0 | 62.5 | 2.3 | 1.3 |
| 2 (Comparative) | 177 | 24.6 | | 22.6 | 0.5 | 0.2 |
| 3 (Inventive) | 204 | 86.6 | 7.2 | 69.4 | 6.6 | 2.6 |
| 4 (Comparative) | 204 | 73.6 | | 66.3 | 4.7 | 0.8 |
| 5 (Inventive) | 232 | 93.7 | 4.9 | 65.8 | 19.0 | 4.7 |
| 6 (Comparative) | 232 | 85.3 | | 75.8 | 6.2 | 1.5 |

$^a$Percent conversion of cyclohexene to products
$^b$Cyclohexyl mercaptan - mole percent in crude reaction mixture.
$^c$Dicyclohexyl sulfide - mole percent in crude reaction mixture.
$^d$Dicyclohexyl disulfide - mole percent in crude reaction mixture.
$^e$Recovered carbon disulfide - mole percent in crude reaction mixture.

The data in Table I show that at each of the 3 temperatures the inventive runs employing carbon disulfide give higher conversion of cyclohexene to products and higher total amount of cyclohexyl mercaptan, dicyclohexyl sulfide and dicyclohexyl disulfide than the comparative runs which contained no carbon disulfide. The inventive runs likewise show that a significant portion of the charged carbon disulfide was recovered (9.1 mole percent based on cyclohexene and carbon disulfide was charged) and hence was not consumed in the reaction. The fact that less carbon disulfide was recovered than charged can be explained by the high volatility of carbon disulfide; i.e., in the venting of unreacted hydrogen sulfide gas some carbon disulfide could have been lost.

It is also noteworthy that at higher temperatures the selectivity of the inventive runs to cyclohexyl mercaptan is lower than in the comparative runs. Therefore one who chooses to operate a process at higher temperatures and to produce a thiol, such as cyclohexyl mercaptan, as final product could use the process of this invention to obtain the thiol and then use well-known prior art processes to prepare additional thiol from the by-products, dicyclohexyl sulfide and dicyclohexyl disulfide, by treatment, for example, with hydrogen sulfide and/or hydrogen over sulfactive catalysts.

I claim:

1. In the preparation of mercaptans by contacting a reaction mixture of hydrogen sulfide and ethylenically unsaturated compounds in the presence of a sulfactive catalyst a method for increasing the total conversion of reactants to mercaptans comprises adding carbon disulfide to the reaction mixture in a molar ratio of hydrogen sulfide to carbon disulfide of from about 5/1 to about 30/1.

2. The method of claim 1 wherein the ethylenically unsaturated compounds are represented by the general formula:

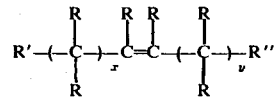

wherein $x$ and $y$ are independently 0 or integers having values of from 1 to 5; wherein the R groups are independently selected from the group consisting of hydrogen and alkyl, cycloalkyl and aryl radicals, or combinations thereof such as alkaryl, aralkyl and the like preferably having 1 to 8 carbon atoms; R' and R'' are independently selected from the group consisting of hydrogen and alkyl radicals having 1 to 5 carbon atoms, and together can form a covalent bond, thus producing a ring, with the proviso that when a covalent bond is formed the sum of $x$ and $y$ is at least 3; and wherein the total number of carbon atoms in the ethylenically unsaturated compounds will not exceed 20.

3. The method of claim 2 wherein the reaction is carried out at temperatures ranging from about 100° to about 350°C and pressures are from about 100 to about 5000 psig.

4. A method of claim 1 wherein an inert diluent chosen from among aliphatic, cycloaliphatic and aromatic hydrocarbons is present in the reaction mixture in a range of about 10 to about 75 weight percent of a solution of the olefin in the diluent.

5. The method of claim 3 wherein the olefin is cyclohexene and the mercaptan produced is cyclohexyl mercaptan.

* * * * *